United States Patent [19]

Enjolras

[11] Patent Number: 5,656,278
[45] Date of Patent: Aug. 12, 1997

[54] DERMATOLOGICAL AND COSMETIC COMPOSITIONS

[75] Inventor: Odile Enjolras, Meudon, France

[73] Assignee: The Boots Company plc, Nottingham, England

[21] Appl. No.: 546,371

[22] Filed: Oct. 20, 1995

Related U.S. Application Data

[63] Continuation of Ser. No. 312,812, Sep. 27, 1994, abandoned.

[30] Foreign Application Priority Data

Sep. 30, 1993 [FR] France .................................... 93 11641

[51] Int. Cl.$^6$ .................................................. A61K 1/48
[52] U.S. Cl. ...................... 424/401; 424/59; 514/844; 514/846; 514/847; 514/937; 514/938; 514/943
[58] Field of Search ................... 424/401, 59; 514/844, 514/846, 847, 937, 938, 943

[56] References Cited

FOREIGN PATENT DOCUMENTS

0556957  2/1990  European Pat. Off. .
9001323  8/1993  WIPO .

*Primary Examiner*—Jyothsna Venkat
*Attorney, Agent, or Firm*—Nikaido, Marmelstein, Murray & Oram LLP

[57] ABSTRACT

A dermatological or cosmetic composition for skin care containing 0.01 to 30% by weight of at least one ceramide and 1 to 15% by weight of linoleic acid useful for restoring the barrier function of the stratum corneum of dry or very dry skin.

8 Claims, 1 Drawing Sheet

FIG. 1

DERMATOLOGICAL AND COSMETIC COMPOSITIONS

PRIOR APPLICATION

This application is a continuation of U.S. patent application Ser. No. 312,812 filed Sep. 27, 1994, now abandoned.

STATE OF THE ART

Water represents 70% of human body weight and with regard to the skin, the dermis represents 15 to 18% of this water. Its content is of the order of 70% and the water content of the epidermis varies considerably with the depth and the type of layer considered. The Malpighian layer (prickle-cell layer of the epidermis above the basal layer) also contains 70% water. As for the horny layer (or Stratum Corneum), it contains 10 to 13% water.

The normal horny layer (orthokeratosic) of a normal epidermis is a layer of non-nucleated cells which is conveniently illustrated according to the Elias model: a wall of bricks, the corneocytes, protein bricks filled with keratin incorporated in the corneal protein envelope (corneal envelope made of several proteins: keratolinin, involucrin, loricrin . . . ), bricks, sealed by an inter-cellular lipidic cement, constituted by archeolayers of lamellar lipids, the ceramides.

The hygroscopic power of the corneocytes and their hydrophilicity are linked to the existence of NMF's (or Natural Moisturizing Factor). These corneocyte moisturizing factors originate from the disintegration by proteolysis of epidermal proteins rich in histidine stored in the keratohyalin granules (filaggrin→NMF). The NMF's are rich in amino acids, lactic acid, pyrrolidone carboxylic acid, urea, etc. These substances take up water from the external medium towards the interior of the corneocytes.

The ceramides, basic sphingolipids, are synthesized in the Odland bodies and discharged into the extra-cellular spaces at the upper part of the granular layer. The ceramides are lipids in lamellar double layers, relatively rigid, whereas the phospholipids of the membranes of the Malpighian layer are fluid. Therefore, they provide the cohesion between the corneocytes, cells which do not have these anchorage structures that are the desmosomes, at the level of the living epidermis.

The ceramides create a layered inter-corneocyte system, a veritable trellis that can be seen by the electron microscope after cryofracture of the stratum corneum. The quasi-crystalline structure of the ceramides gives them a great mechanical stability, an impermeability to water and a resistance to oxidation on contact with the air. The ceramide trellis fixes the corneocytes and provides the cutaneous surface with its imperviousness and its cohesion.

The lipids of the corneal barrier control the losses of water through the epidermis: if they decrease, the losses increase. This flow of water loss through the epidermis is a minimum flow of water not retained by the organism which by crossing the epidermis (non vascularized), supplies it with nutrients and oxygen. If this flow increases, the skin becomes rough and dry.

The lipids of the horny layer protect the NMF's and the Elias model becomes a wall of hydrophilic protein bricks (the corneal cells) sealed by a hydrophobic ceramide lipidic cement. Any alteration to one of these constituents will alter this hydrophilic-lipophilic surface barrier and will modify the exchanges of water and the surface desquamation. The skin will suffer from xerosis.

At least 7 types of ceramides are known in the human skin, which are the following:

N-(ω-acyloxy)-acylsphingosine

N-acylsphingosine

N-acylphytosphingosine

N-(α-hydroxy) acylsphingosine

N-(α-hydroxy) acylsphingosine

Non-definitive precise chemical configuration

N-(α-hydroxy) acylphytosphingosine

Many products exist on the market containing ceramides. In fact, ceramides can be extracted from animals brains, particularly oxen, or they can be extracted from vegetation such as wheat, or they can also be extracted from yeasts or they can also be produced by genetically modified microorganisms.

The ceramides are usually a mixture of glycosyl-ceramides and true ceramides. Synthetic ceramides also exist whose structure is identical to natural ceramides; synthetic molecules also exist such as ceramide HO3 from the SEDERMA Company whose structure is close to that of natural ceramides.

Many cosmetic products launched on the market contain ceramides. These are very varied and come from the different sources mentioned above. It has been shown particularly that a cream containing glycosyl-ceramides of bovine origin or ceramide HO3 enabled the barrier function to be restored.

However, if it is good to replace the natural ceramides on a dry skin which lacks them, it is necessary to question the origin of the ceramide deficit of this dry or very dry skin. It may be a delipidation by excess washing, numerous baths, perspiration-drying or too frequent use of inappropriate make-up removers. In all cases, the Odland bodies which synthesize the ceramides would have to take action and discharge these organized lipidic layers into the stratum corneum. But stress on the keratinocytes (heat, sun, chemical or bacteriological attacks) and ageing can reduce the speed of repair.

On the other hand, many tests have been carried out both in dermatology and in cosmetics, incorporating oils rich in linoleic acid for topical treatment of dry and very dry skin, such as skin suffering from xerosis, ichthyosis, atopy, psoriasis, as shown by GUILHOU (Montpellier) in a recent review of clinical tests which were carried out (Ann. Dermatol. Venerol., (1992), Vol. 119, pp. 233–239), the results are variable, sometimes positive, sometimes non-existent (vis-a-vis a placebo). The activity of linoleic acid and the other essential fatty acids is well enough understood in the production of prostaglandins and leucotrienes. But, this mechanism alone cannot explain the restoration of the barrier function.

OBJECTS OF THE INVENTION

It is an object of the invention to provide improved dermatological and cosmetic compositions.

It is another object of the invention to provide a novel method for restoring the barrier function of the stratum corneum of dry or very dry skin.

These and other objects and advantages of the invention will become obvious from the following detailed description.

THE INVENTION

The novel dermatological and cosmetic compositions of the invention contain an effective amount of a mixture of at least one ceramide and linoleic acid.

Study of the effects produced by the use in cosmetics and in dermatology of such compositions shows that dry or very dry skin, pathological or otherwise, is immediately improved. An initial immediate substitute to the barrier function is supplied by the ceramides, and at the same the necessary elements for a resumption of the metabolism is supplied to dry or very dry skin.

Such cosmetic or dermatological compositions are therefore intended to strengthen the barrier function of the stratum corneum of dry and very dry skin. Remarkable results have been obtained by such a combination of ceramides and linoleic acid as shown by the results described hereafter.

The ceramides are extracted from the brains of mammals, particularly oxen, from vegetation, particularly wheat, from microorganisms, particularly yeasts or from genetically modified microorganisms. The ceramides can be mixtures of ceramides and glycosyl-ceramides and the ceramides can be of synthetic or semi-synthetic origin. The ceramides of the invention can be molecules whose structure is close to that of the natural ceramides such as ceramide HO3 or myristyl palmitamido-serinate, 2 molecules from the SEDERMA Company.

In the compositions, the ceramides are preferably selected from ceramides (mixed with glycosyl ceramides) of animal origin (particularly from ox brain, milk), of vegetable origin (particularly wheat), or extracted from microorganisms such as yeasts, or genetically modified microorganisms, or also from synthetic, semi-synthetic ceramides, or ceramides similar to natural ceramides such as ceramide HO3 or DERMACERIDE (myristyl palmitamido-serinate), two compounds from the SEDERMA Company. The HO3 has the formula:

CERAMIDE HO3

The ceramide content of the preparations of the invention can vary from 0.01% to 30%, preferably from 0.1 to 15%, and more preferably from 0.1 to 1%.

The linoleic acid source may be a vegetable oil or a mixture of two or more vegetable oils rich in linoleic acid or a phospholipid rich in linoleic acid. Preferably, the linoleic acid source is a vegetable oil or a mixture of two or more vegetable oils rich in linoleic acid containing at least 20% linoleic acid and more preferably 50%.

The linoleic acid can be supplied by an oil containing at least 20% of this fatty acid such as grapeseed oil, peanut oil, apricot seed oil, sweet almond oil, hazelnut oil, cottonseed oil, rice bran oil, sesame oil, cherry seed oil, borage oil, rapeseed oil and preferably an oil containing more than 50% linoleic acid such as evening primrose oil, sunflower seed oil, safflower oil, soya oil, wheatgerm oil, passion flower oil, mawseed oil, linseed oil. As a source of linoleic acid, wheatgerm oil is preferred.

The linoleic acid can also be obtained by mixing two or more of these oils. A semi-synthetic oil can also be used: triglyceride enriched with linoleic acid. The content of oil rich in linoleic acid of the preparations can vary from 1 to 20%, preferably 2 to 10%. The linoleic acid content of the preparations can vary from 1 to 15%, preferably from 1 to 10% by weight.

The linoleic acid can also be supplied by phospholipids of vegetable or animal origin, particularly egg and soya lecithins, more or less oil-free, more or less enriched with phosphatridinyl choline, or enriched with phosphatidyl ethanolamine or enriched with phosphatidylinositol, a phospholipid complex originating from lecithin of oil-free soya containing 55 to 58% of linoleic acid. The content of phospholipids rich in linoleic acid of the preparations can vary from 1 to 30%, preferably from 2 to 10%.

The content of oil rich in linoleic acid can vary from 1 to 20%, preferably from 2 to 10%, that the content of phospholipids rich in linoleic acid can vary from 1 to 30%, preferably from 2 to 10%.

The compositions of the invention can optionally also contain hydrosoluble or liposoluble active ingredients, filters, screens for solar radiation, vitamin extracts, perfumes, preservatives, anti-oxidants or, coloring agents. In particular, the hydrosoluble active ingredients can be moisturizing agents or regenerating agents or anti-inflammatories and the liposoluble active ingredients can be healing, nutritional or anti-inflammatory agents.

Sunscreens and sun reflectors can also optionally be added to the cosmetic and dermatological compositions of the invention to give them a protective power vis-a-vis solar radiation. When these additives are insoluble in oily and aqueous phases, they constitute a supplementary phase. They are chosen for example from the following products: perfluoroethers such as FOMBLIN (R) from the MONTE-CATINI Company, insoluble pigments such as titanium oxide, futile titanium oxide, anatase titanium oxide, pyrogenated titanium oxide such as P 25 (R) from Degussa, micronized titanium oxide in SUN VEIL (R) from Ikeda, titanium oxide surface-treated with silicones or amino acids or lecithin or metallic stearates, iron oxide; iron oxide treated on the surface by silicones, or by amino acids or by lecithin or by metallic stearates, zinc oxide, micronized zinc oxide such as UFZO (R) from Cosmo Trends Corporation and/or mica covered with titanium oxide.

Preferably, one or more hydrosoluble active ingredients are selected from sodium lactate (keratolytic and moisturizing), extracts of Hafnia biolysate (anti-inflammatory and growth factors), extracts of Klebsiella pneumoniae biolysate (anti-elastase and anti-collagenase) and hydrosoluble sunscreens (protective against UVA and UVB solar radiation).

Thus, in a preferential manner, the hydrosoluble sunscreens and/or the hydrosoluble active ingredients can be chosen from neutralized 2-phenyl benzimidazol 5-sulfonic acid, neutralized 2-hydroxy 4-methoxybenzophenone 5-sulfonic acid, ascorbic acid, caffeine benzoate, phytic acid, mucic acid, hydrolysates of vegetable proteins, polyglucan, Mexican mimosa extract, chitosan, marine animal serum, hirudin extract, meristem extract, procyanodolic oligomers, yeast extracts, panthenol, centella asiatica extract and glycyrrhetinic acid.

As an illustration of such a use of such hydrosoluble active ingredients, but without however limiting the usable quantities of these active ingredients, the following examples can be given in which the preferred percentages are expressed relative to the final complete formula:

neutralized 2-phenyl benzimidazol 5-sulfonic acid: 0.5 to 8%, neutralized 2-hydroxy 4-methoxybenzophenone 5-sulfonic acid: 0.5 to 5%, ascorbic acid: 0.5 to 10%, caffeine benzoate: 0.1 to 5%, phytic acid: 0.1 to 5%, mucic acid: 0.1 to 5%, hydrolysates of vegetable proteins: 0.1 to 10%, polyglucan: 0.1 to 5%, Mexican mimosa extract: 0.5 to 20%, chitosan: 0.5 to 20%, marine animal serum: 0.1 to 3%, hirudin extract: 0.5 to 10%, meristem extract: 0.1 to 5%, procyanodolic oligomers: 0.05 to 3%, yeast extracts: 0.05 to 3%, panthenol: 0.05 to 5%, centella asiatica extract: 0.05 to 3%, glycyrrhetinic acid: 0.05 to 2%.

The liposoluble active ingredients in the oily phase are selected from vitamin A palmitate, liposoluble sunscreens, nonsaponifiable matter of vegetable origin, tocopherol acetate, natural tocopherols, farnesol.

In a preferential manner but without however limiting the invention, it can be indicated that the liposoluble sunscreens can be selected from octyl methoxycinnamate, isoamyl methoxycinnamate, octyl dimethyl paba, octyl salicylate, butyl methoxydibenzoyl methane, benzophenone 3, octyl triazone, ethyl 4-polyethoxy 5-aminobenzoate, isopropyl 4-dibenzoyl methane.

The nonsaponifiable matter of vegetable origin can be chosen from the nonsaponifiable matter of corn, karite, soya and avocado and the oily mixture containing xymenic acid can be Xymenoil which contains 50% of this acid.

As an illustration of such a use of such liposoluble active ingredients, the following examples can be given in which the preferred percentages are expressed relative to the final complete formula:

vitamin A palmitate: 500 to 10,000 IU/g,
liposoluble sunscreens: octyl methoxycinnamate: 0.5 to 10%, isoamyl ethoxycinnamate: 0.5 to 10%, octyl dimethyl 25 paba: 0.5 to 8%, octyl salicylate: 0.5 to 5%, butyl methoxy-dibenzoyl methane: 0.5 to 5%, benzophenone 3: 0.5 to 10%, octyl triazone: 0.5 to 5%, ethyl 4-polyethoxy aminobenzoate: 0.5 to 10%, isopropyl 4-dibenzoyl methane: 0.5 to 5%,
nonsaponifiable matter of corn, karite, soya or avocado: 0.1 to 3%,
Ximenoil (R): 0.1 to 5%, essential extract of sesame oil: 0.1 to 4% peroxidized corn oil: 0.1 to 10%, tocopherol acetate: 0.05 to 7%, natural tocopherols: 0.05 to 5%, farnesol: 0.05 to 5%.

The active ingredients of the invention can be incorporated with excipients usually employed in these dermatological or cosmetic compositions. For each form, suitable excipients are available which excipients must have all the usually-required qualities. They must be endowed with a great affinity for the skin, be perfectly well tolerated, stable and have an adequate consistency allowing an easy and agreeable use.

As an example of excipients which can be used, there can be mentioned in particular the following oily phase excipients: hydrocarbons such as diisopropylcyclohexane or hydrogenated polyisobutene, silicone oils, natural triglycerides, semi-synthetic or synthetic triglycerides, vegetable waxes such as carnauba wax, animal waxes such as beeswax, or mineral waxes such as ozokerite, fatty acids such as stearic acid, fatty alcohols such as cetyl alcohol or isocetyl alcohol, fatty acid esters such as octyl palmitate, fatty alcohol esters, fatty acid amides, lanolin and its usual derivatives such as lanolin alcohols, lanolin acids, hydroxylated or hydrogenated lanolin, mineral oils such as vaseline oil, vegetable oils such as avocado or jojoba oil, hydrogenated vegetable oils such as hydrogenated palm oil.

Examples of aqueous phase excipients are moistening agents like glycerine, propylene glycol, PEG400, sorbitol, gelatinizing agents such as carboxyvinyl polymers, xanthan gum, guar gum, modified carboxyvinyl polymers such as PEMULEN, sclerosium gum, CMC's, modified CMC's, hydroxyethylcelluloses, hydroxypropyl-celluloses, modified hydroxyethylcelluloses such as AMERCELL HM1500 and thickeners such as VEEGUM.

Among the excipients, surfactants are frequently used such as sorbitan esters like sorbitan stearate, oxyethylenated sorbitan esters such as sorbitan palmitate POE, sucrose esters such as sucrose cocoate, oxyethylenated or non-oxyethylenated glucose or methylglucose esters such as methylgluceth-20 or methyl-glucose sesquistearate, neutralized acyl phosphates such as potassium cetylphosphate, ethoxylated fatty acids such as ethoxylated stearic acid, ethoxylated fatty alcohols such as ethoxylated stearyl alcohol, more or less oil-free lecithins of egg or soya, hydrogenated or not, of ethoxylated vegetable sterols.

The excipients can also contain wetting agents, preservatives such as methylparaben, biosol, bronopol, perfumes, coloring agents or fillers such as talc or polymethacrylate.

The different cosmetic or dermatological forms mentioned above can be obtained according to the usual methods used in this domain. The dermatological and cosmetic compositions can be solid or liquid or in paste form and be presented in the dermatological and cosmetic forms commonly used such as creams or gels in pots or in tubes, lotions in glass or plastic bottles and optionally in dropping bottles, phials, fluids, ointments. They are prepared according to the usual methods.

Preferably, pharmaceutical compositions are characterized in that they are presented in the form of liquid or solid preparations for topical use and may be preferably presented in one of the following forms:

fatty gels, simple water-in-oil emulsions, simple oil-in-water emulsions, multiple emulsions, for example:

water-in-oil-in-water or oil-in-water-in-oil, a triple water-in-oil-in-water emulsion, a triple oil-in-water-in-oil emulsion, an oil-in-water emulsion containing liquid crystals, complex emulsions containing liquid crystals forming lipid double layers surrounding the oily phases, pseudo-emulsions (dispersion of an oily phase or a water-in-oil emulsion in a gelatinized aqueous phase, without traditional surfactants), oil-in-water or water-in-oil micro-emulsions, emulsions containing dispersed oil phases, different from each other and insoluble in each other, a pseudo-emulsion or dispersion of an oily phase dispersed in an aqueous phase and stabilized with Lubragel, Pemulen, Hypan, xanthan gum, CMC, hydroxyethyl cellulose, Amigel, Polyvinylpyrrolidone, Amercell HM1500, or a mixture of two or more of these gelatinizing agents.

A particular subject of the present invention is the use of dermatological or cosmetic compositions, characterized in that they contain ceramides and a linoleic acid source, for restoring the barrier function of the stratum corneum of dry and very dry skin.

The novel method of the invention for restoring the barrier function of the stratum corneum of dry or very dry skin comprising applying to the said skin an effective amount of a dermatological or cosmetic composition for skin care containing 0.01 to 30% by weight of at least one ceramide and 1 to 15% by weight of linoleic acid.

In the following examples, there are described several preferred embodiments to illustrate the invention. However, it is to be understood that the invention is not intended to be limited to the specific embodiments.

EXAMPLE 1

Cream I

The following oily phase was heated to 70° C.:

| | |
|---|---|
| stearamidopropyl PG-dimonium chloride phosphate (CTFA name) | 3.0 g |
| cocamidopropyl PG-dimonium chloride phosphate | 1.0 g |

| (CTFA name) | |
|---|---|
| cetyl alcohol | 3.0 g |
| myristyl myristate | 5.0 g |
| hydrogenated polyisobutene | 2.0 g |
| karite butter | 2.0 g |
| propylene glycol stearate | 3.0 g |
| silicone oil | 2.0 g |
| wheatgerm oil containing at least 50% of linoleic acid | 5.0 g |
| anti-oxidant | 0.2 g |
| ceramide HO3 (SEDERMA) | 0.2 g |

In addition, the following aqueous phase was prepared and was heated to 70° C.:

| demineralized water | 61.08 g |
|---|---|
| glycerine | 10.0 g |
| modified hydroxy ethylcellulose | 0.5 g |
| PVP | 1.0 g |
| preservatives | 0.52 g |

An O/W emulsion was produced by vigorously mixing the two phases at 90° C. for 10 minutes and then they were cooled slowly with moderate stirring. 0.5% of perfume was added at 45° C. and then cooling was continued to 25° C. to obtain a cationic O/W emulsion designated as cream I, having an ivory-white color, being agreeable to the touch, having a pH of 5.6 and Brookfield viscosity of 24,000 cPs.

Moisturizing Test

The moisturizing test described hereafter was carried out to compare the activity of cream I of the invention, prepared as indicated in Example 1 which contained ceramides and linoleic acid, with the respective activities of two creams II and III such that cream II contained ceramides but no linoleic acid and cream III contained linoleic acid but no ceramides.

The following results obtained in the moisturizing test show the superiority of cream I over creams II and III.

Creams II and III were prepared as follows:

Cream II

The process was carried out as in Example 1, replacing the wheatgerm oil with a caprylic/capric saturated triglyceride. The following oily phase was heated to 70° C.:

| stearamidopropyl PG-dimonium chloride phosphate (CTFA name) | 3.0 g |
|---|---|
| cocamidopropyl PG-dimonium chloride phosphate (CTFA name) | 1.0 g |
| cetyl alcohol | 3.0 g |
| myristyl myristate | 5.0 g |
| hydrogenated polyisobutene | 2.0 g |
| karite butter | 2.0 g |
| propylene glycol stearate | 3.0 g |
| silicone oil | 2.0 g |
| caprylic/capric saturated triglyceride | 5.0 g |
| anti-oxidant | 0.2 g |
| Ceramide HO3 (SEDERMA) | 0.2 g |

In addition, the following aqueous phase was prepared and was heated to 70° C.:

| demineralized water | 61.08 g |
|---|---|
| glycerine | 10.0 g |
| modified hydroxy ethylcellulose | 0.5 g |
| PVP | 1.0 g |
| preservatives | 0.52 g |

As in Example 1, an O/W emulsion was produced by vigorously mixing the two phases at 90° C. for 10 minutes. They were then cooled slowly with moderate stirring. 0.5% of perfume was added at 45° C. and then cooling was continued to 25° C. to obtain a cationic O/W emulsion, designated cream II which therefore contained ceramides but no linoleic acid.

Cream III

The process was carried out as in Example 1 and the following oily phase was heated to 70° C.:

| stearamidopropyl PG-dimonium chloride phosphate (CTFA name) | 3.0 g |
|---|---|
| cocamidopropyl PG-dimonium chloride phosphate (CTFA name) | 1.0 g |
| cetyl alcohol | 3.0 g |
| myristyl myristate | 5.0 g |
| hydrogenated polyisobutene | 2.0 g |
| karite butter | 2.0 g |
| propylene glycol stearate | 3.0 g |
| silicone oil | 2.0 g |
| wheatgerm oil containing at least 50% of linoleic acid | 5.0 g |
| anti-oxidant | 0.2 g |

In addition, the following aqueous phase was prepared and was heated to 70° C.:

| demineralized water | 61.08 g |
|---|---|
| glycerine | 10.0 g |
| modified hydroxy ethylcellulose | 0.5 g |
| PVP | 1.0 g |
| preservatives | 0.52 g |

As in Example 1, an O/W emulsion was produced by vigorously mixing the two phases at 90° C. for 10 minutes and they were then cooled slowly with moderate stirring. 0.5% of perfume was added at 45° C. and then cooling was continued to 25° C. to obtain a cationic O/W emulsion designated cream III which contained linoleic acid but no ceramides.

Protocol of the Moisturization Test

1. Particpants

A dermatologist selected 4 adults, 3 women and 1 man, caucasian, healthy, 25 to 50 years old. These participants under-took to follow their usual routine as regards washing, but abstained from using any cosmetic care product on their arms.

2. Protocol for Application

Measurement and application area:

Forearm, inner or outer area of 10 cm$^2$

Area A (the highest) right arm, CREAM II

Area B (in the middle) right arm, CREAM I

Area C (low down) right arm, without treatment (control area) Area

D (the highest) left arm, CREAM III

Area E (in the middle) left arm, CREAM I

Area F (low down) left arm, without treatment (control area)

Application dose:

2 mg/cm$^2$ or 20 mg/10 cm$^2$

Protocol for application:

On clean skin, with massaging for a few seconds using a finger covered with a rubber finger guard.

Frequency of application:

5 applications: over a maximum of 8 days, once a day.

3. Measurements

The degree of moisturization of the horny layer at the stratum corneum was determined using a corneometer and in each area, 3 measurements were taken and the average was calculated.

The principle of the apparatus is based on the measurement of the dielectric properties of the skin and the reading was made directly with the apparatus which measured, using a capacitor, the electrical capacitance of a portion of skin placed under the probe. A measurement was taken before treatment and then after the first application (at least 10 minutes after, at most 30 minutes after). The other measurements were taken on the other days at about the same time, before new applications when there were any. Measurements were continued to be taken every weekday for about 10 days after the last application.

The differences obtained were monitored by application of creams I, II and III on each arm, the 3rd area serving as the control to verify the skin's own development. These differences were monitored for the period of time when the product was applied and after treatment had stopped. For each measurement, the time, the ambient temperature and the degree of humidity of the room where the measurements were taken were noted.

4. Results

They were recorded on sheets, one per participant and each sheet contained all the information relating to the measurements: date, time, temperature of the room and degree of humidity, the 3 measurements taken on each area and the average of these 3 measurements.

Weighting

Each average of each area was modified by 2 weightings: a plus or minus percentage variation, which took into account the measurement deviation observed on D0 before application between the areas intended for the application and the control areas of the same arm. This weighting applied to all the measurements of each area. A second weighting was carried out for the measurements on a given day, taking into account the difference observed between the measurement of the control area on this day and that of D0. This means that the variations between areas and the actual variations of the skin of each subject were equalized.

Results

The weighted results were used to calculate the moisturization differences produced by cream I of the invention which contained ceramides and linoleic acid, with cream II which contained ceramides but no linoleic acid, and cream III which contained linoleic acid but no ceramides. The arithmetic means of these differences were calculated and the means of D11 of subject AF were integrated with the means of D13 of the other subjects.

Figure 1:
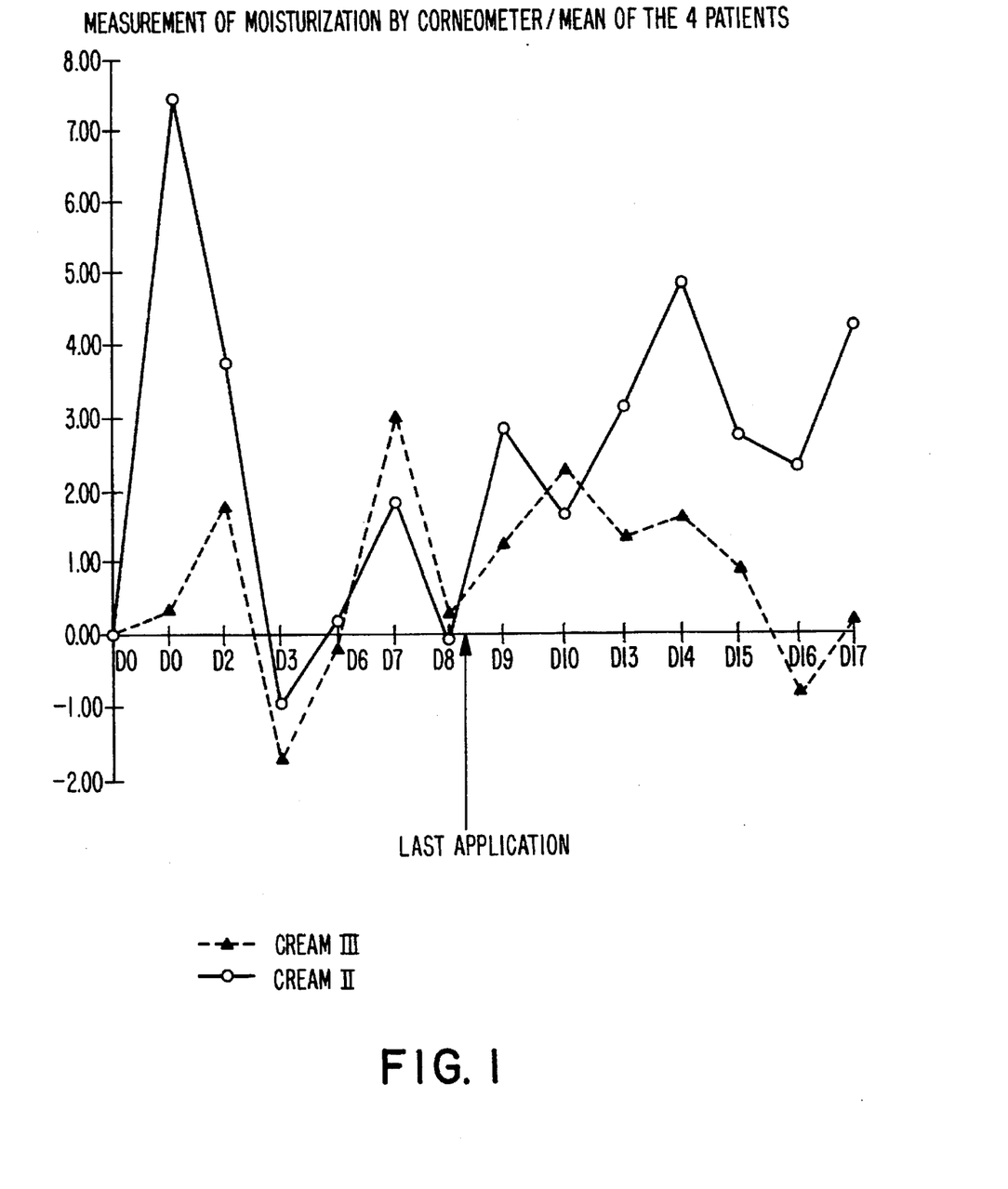

Tables Ia and Ib which indicate the results obtained by the moisturization test described above show that the deviations from the mean are almost always positive, particularly after treatment had stopped. Tables Ia and Ib as well as figure I which illustrates the results, show that the combination of ceramides and linoleic acid in a moisturizing cream produces a moisturizing effect greater than that of the creams which only have one of the ingredients.

The results indicated in tables Ia and Ib show particularly that at least up to 10 days after the last application carried out on the 8th day (D8), the moisturization produced by the application of cream I was still greater (mean>0) than that produced by the application of creams II and III. In Tables Ia and Ib, it can be seen that the "mean" column was almost always positive, which means that the moisturization rate at the place treated by the complete cream was greater than the moisturization rate of the incomplete creams, which demonstrates the advantage of combining ceramides and a linoleic acid source in a moisturizing cream.

TABLE Ia

Compilation of the weighted results

Subjects treated by creams I and II

| D No. | 1 | 2 | 3 | 4 | MEAN |
|---|---|---|---|---|---|
| D0  | 0.00  | 0.00  | 0.00  | 0.00   | 0.00  |
| D'0 | 17.83 | −8.23 | −1.46 | −6.71  | 0.36  |
| D2  | 6.63  |       |       | −3.00  | 1.82  |
| D3  | −6.40 | 4.05  | −1.13 | −3.22  | −1.68 |
| D6  |       |       | −0.37 | 0.02   | −0.18 |
| D7  | 2.38  | 7.42  | −0.77 |        | 0.32  |
| D8  |       |       | 1.59  | −1.84  | 0.32  |
| D9  | 5.61  | −0.41 | 0.96  | −1.15  | 1.25  |
| D10 | 7.31  | 1.60  | 0.91  | −0.63  | 2.30  |
| D13 | 2.22  | 3.04  | 1.38  | −1.37  | 1.32  |
| D14 | 6.22  | 2.05  | −1.66 | −0.10  | 1.63  |
| D15 | 2.83  | 0.78  | 2.82  | 2.92   | 0.88  |
| D16 | 4.12  | 1.53  | −3.52 | −5.52  | −0.85 |
| D17 | 3.16  | 0.17  | −3.86 | 1.31   | 0.20  |
| TOTAL | 51.91 | 13.59 | −5.50 | −25.13 | 0.80 |

TABLE Ib

Compilation of the weighted results

Subjects treated by creams I and III

| D No. | 1 | 2 | 3 | 4 | MEAN |
|---|---|---|---|---|---|
| D0  | 0.00  | 0.00  | 0.00  | 0.00  | 0.00  |
| D'0 | 6.16  | 0.65  | 9.95  | 13.00 | 7.44  |
| D2  | 9.56  |       |       | −2.10 | 3.73  |
| D3  | 4.12  | −5.63 | 1.53  | −3.86 | −0.96 |
| D6  |       |       | 0.42  | −0.06 | 0.18  |
| D7  | 8.15  | −3.55 | 0.95  |       | 1.85  |
| D8  |       | −1.10 | 0.41  | 0.38  | −0.10 |
| D9  | 16.29 | −0.61 | −2.45 | −1.80 | 2.86  |
| D10 | 9.31  | 2.45  | −3.06 | −2.06 | 1.66  |
| D13 | 6.41  | 7.27  | 1.82  | −3.00 | 3.13  |
| D14 | 10.10 | 6.01  | 3.67  | −0.57 | 4.80  |
| D15 | 9.57  | 4.57  | 1.81  | −5.03 | 2.73  |
| D16 | 3.04  | 6.72  | 1.41  | −2.00 | 2.29  |
| D17 | 5.45  | 2.74  | 2.29  | 6.31  | 4.20  |
| TOTAL | 88.16 | 19.52 | 18.75 | −0.79 | 2.60 |

EXAMPLE 2

Face cream

A face cream was prepared as in Example 1 and was constituted by:

| | |
|---|---|
| ceramide | 0.5 g |
| evening primrose oil | 2.0 g |
| potassium alkyl phosphate | 2.0 g |
| ethyl hexyl palmitate | 8.0 g |

-continued

| | |
|---|---|
| hydrogenated lanolin | 5.0 g |
| fatty acid triglycerides | 4.0 g |
| sorbitan stearate | 1.0 g |
| neutralized carboxyvinyl polymer | 0.4 g |
| preservatives | 0.4 g |
| aromatic composition | 0.4 g |
| purified water SQF | 100.0 g |

EXAMPLE 3

Body cream

A body cream was prepared as in Example 1 and was constituted by:

| | |
|---|---|
| wheat ceramide | 0.2 g |
| glycerol stearate | 4.0 g |
| sorbitan palmitate | 6.0 g |
| perhydrosqualene | 5.0 g |
| diisopropyl-cyclohexane | 7.0 g |
| sunflower oil | 9.0 g |
| glycerine | 5.0 g |
| preservatives | 0.35 g |
| aromatic composition | 1.0 g |
| purified water SQF | 100.0 g |

EXAMPLE 4

Sun milk

A sun milk cream was prepared as in Example 1 and was constituted by:

| | |
|---|---|
| milk ceramide | 0.1 g |
| sunscreens | 5.0 g |
| vaseline oil | 10.0 g |
| ketearyl octanoate | 4.0 g |
| oil free soya phospholipids | 5.0 g |
| silicone oil | 2.5 g |
| P.O.E. cetyl ether | 2.0 g |
| sorbitan stearate | 1.0 g |
| preservatives | 0.35 g |
| aromatic composition | 0.5 g |
| purified water SQF | 100.0 g |

EXAMPLE 5

Multiple emulsion

The following aqueous phase, called the internal aqueous phase, was heated to 80° C.:

| | |
|---|---|
| demineralized water | 26.52 g |
| methylparaben | 0.1 g |
| magnesium sulfate | 0.28 g |
| glycerine 30° B | 0.8 g |
| O-cymen-5-ol | 0.04 g |

The following oily phase was heated separately:

| | |
|---|---|
| glyceryl isostearate | 2 g |
| polyoxyethylenated hydrogenated ricin oil (7 mols) | 0.2 g |
| soya oil | 8.2 g |
| propylparaben | 0.06 g |
| volatile silicone oil | 1.6 g |
| ceramide HO3 | 0.5 g |

The aqueous phase was dispersed in the oily phase at 80° C. by stirring vigorously for 5 minutes and then, the dispersion was cooled slowly to 25° C. This primary water/oil emulsion was dispersed in the following aqueous phase, called the external aqueous phase, mixing gently at ambient temperature:

| | |
|---|---|
| demineralized water SQF | 100.0 g |
| Lubragel MS (R) | 15.0 g |
| Carbopol 980 (R) | 0.03 g |
| tetrasodium EDTA | 0.054 g |
| methylparaben | 0.216 g |
| imidazolidinyl urea | 0.216 g |
| pure sodium hydroxide | 0.125 g |

EXAMPLE 6

Twin-phase emulsion

The following oily phase was heated to 80° C.:

| | |
|---|---|
| stearyl alcohol | 1.0 g |
| cetyl alcohol | 2.0 g |
| ketearyl octanoate | 4.0 g |
| polysorbate 60 | 4.0 g |
| sorbitan stearate | 4.0 g |
| safflower oil | 6.0 g |
| karite butter | 3.0 g |
| oleyl acetate | 2.0 g |
| silicone oil | 0.5 g |
| tocopherols | 0.05 g |
| ceramide HO3 | 0.5 g |

The following aqueous phase was heated to 80° C.:

| | |
|---|---|
| demineralized water SQF | 100.0 g |
| vinyl carboxy polymer | 0.3 g |
| preservative | 0.7 g |
| Lubragel MS (R) | 5.0 g |
| pure sodium hydroxide | 0.3 g |

The oily phase was dispersed in the aqueous phase and stirring was carried out vigorously for 10 minutes and the emulsion was cooled slowly to 25° C. and perfume was added under moderate stirring:

| | |
|---|---|
| perfume | 0.2 g |

EXAMPLE 7

Water/silicone emulsion

The following oily phase was heated to 60° C.:

| | |
|---|---|
| demineralized water SQF | 100.0 g |
| sodium chloride | 0.8 g |
| pure citric acid | 0.01 g |
| methylparaben | 0.25 g |
| propylene glycol | 2.0 g |
| O-cymen-5-ol | 0.1 g |

The following silicone phase was heated to 60° C.:

| | |
|---|---|
| isocetyl stearate | 3.0 g |
| Arlacel 83 (R) | 0.8 g |
| hydrogenated ricin oil | 0.3 g |

| | |
|---|---|
| Elfacos ST9 (R) | 2.0 g |
| oleyl acetate (anti-lipase) | 0.15 g |
| Silicone DC 3225 (R) (DOW CORNING) | 9.0 g |
| volatile silicone | 4.0 g |
| wheat ceramide | 0.5 g |
| mawseed oil | 3.0 g |

The aqueous phase was dispersed in the silicone phase with moderate stirring for 10 minutes and the emulsion was cooled to 25° C. and perfume was then added:

| | |
|---|---|
| perfume | 0.3 g |

EXAMPLE 8

Emulsion without emulsifier

The following oily phase was heated to 80° C.:

| | |
|---|---|
| wheatgerm oil | 4.0 g |
| polyisobutene | 4.0 g |
| octyl stearate | 4.0 g |
| ceramide HO3 | 2.0 g |

The following aqueous phase was heated to 80° C.:

| | |
|---|---|
| glycerine 30° codex | 3.0 g |
| carboxyvinyl polymer | 0.45 g |
| Lubragel MS (R) | 4.0 g |
| pure sodium hydroxide | 0.055 g |
| preservatives | 0.55 g |
| perfume | 0.20 g |
| demineralized water | 60.0 g |

The oily phase was dispersed in the aqueous phase with very gentle stirring and high shearing for half an hour. The emulsion was then slowly cooled to 45° C., then the following was added with strong stirring:

| | |
|---|---|
| talc | 3.0 g |

When the dispersion of the talc was complete, cooling was continued with slow stirring. When the temperature reached 25° C., the following was added with moderate stirring:

| | |
|---|---|
| perfume | 0.2 g |

EXAMPLE 9

An oil-in-water emulsion was prepared in the following manner. The components of the following oily phase were heated to 80° C.:

| | |
|---|---|
| self-emulsifiable glycerol stearate (Arlacel 165 (R) from the ICI Co.) | 6.0 g |
| cetyl alcohol | 1.0 g |
| ethoxylated soya sterol (Generol 122 E 10 (R) from the Henkel Co.) | 2.0 g |
| mixture of vaseline oil and lanolin alcohol | 3.0 g |

| | |
|---|---|
| (Amerchol L101 (R) from the Amerchol Co.) petrolatum and lanolin alcohol (Amerchol CAB (R) from the Amerchol Co.) | 1.0 g |
| safflower oil | 6.0 g |
| karite butter | 3.0 g |
| propyl paraben | 0.05 g |
| ceramide HO3 | 0.5 g |

In addition, the following aqueous phase was prepared and was also heated to 80° C.:

| | |
|---|---|
| demineralized water | 60.0 g |
| 70% sorbitol | 3.0 g |
| xanthan gum | 0.3 g |
| methylparaben | 0.1 g |

When the xanthan gum was well dispersed, the oily phase was added to the aqueous phase at 80° C., add vigorous stirring was Carried out for 20 minutes. The emulsion formed and then, the stirring was reduced. The emulsion was cooled slowly to 40° C. and then 2 g of water containing 0.15 g of imidazolidinyl urea followed by 0.3 g of perfume, were added to the emulsion.

Various modifications of the composition and method of the invention may be made without departing from the spirit or scope thereof and it is to be understood that the invention is intended to be limited only as defined in the appended claims.

What is claimed is:

1. A dermatological or cosmetic composition for skin care containing an active ingredient consisting essentially of a sufficient amount of a mixture of 0.1 to 15% by weight of ceramide HO3 of the formula

CERAMIDE HO3 and 1 to 15% of a vegetable oil or a mixture of two or more vegetable oils rich in linoleic acid to restore the barrier function of the stratum corneum.

2. A composition of claim 1 wherein the vegetable oil is wheatgerm oil.

3. A composition of claim 1 containing 0.1 to 1% of ceramide HO3.

4. A method of restoring the barrier function of the stratum corneum of dry or very dry skin comprising applying to the said skin an effective amount of a composition of claim 1.

5. The method of claim 4 wherein the composition is in the form of a cosmetic product.

6. The method of claim 4 wherein the vegetable oil is wheatgerm oil.

7. A method of claim 4 wherein the composition has a form selected from the group consisting of a) simple water-in-oil emulsions, or b) simple oil-in-water emulsions, or c) triple water-in-oil emulsions, or d) complex emulsions containing liquid crystals forming lipidic double layers surrounding the oil phases, or e) pseudo-emulsion or dispersion of an oily phase or a water-in-oil emulsion in a gelatinized aqueous phase without surfactants or f) a pseudo-emulsion or dispersion of an oily phase dispersed in an aqueous phase and stabilized with at least one member of the group consisting of modified carboxy vinyl polymers xanthan gum, carboxymethyl cellulose, hydroxyethyl cellulose, polyvinyl-pyrrolidone and modified hydroxyethyl cellulose.

8. A dermatological or cosmetic composition for skin care having a form selected from the group consisting of a) simple water-in-oil emulsion, or b) simple oil-in-water emulsions, or c) triple-water-in-oil-in water emulsion, or d) complex emulsions containing liquid crystals forming lipidic double layers surrounding the oil phase, or e) pseudo-emulsions or dispersions of an oily phase or a water-in-oil emulsion in a gelatinized aqueous phase without surfactants or f) a pseudo-emulsion or dispersion of an oily phase dispersed in an aqueous phase and stabilized with at least one member of the group consisting of modified carboxy vinyl polymers, xanthan gum, carboxymethyl cellulose, hydroxyethyl cellulose, polyvinyl-pyrrolidone and modified hydroxyethyl cellulose and containing an active ingredient consisting essentially of a sufficient amount of a mixture of 0.1 to 15% by weight of ceramide HO3 of the formula and 1 to 15% of a vegetable oil or a mixture of two or more vegetable oils rich in linoleic acid to restore the barrier function of the stratus corneum.

* * * * *